US010245093B2

(12) United States Patent
Dunn

(10) Patent No.: US 10,245,093 B2
(45) Date of Patent: Apr. 2, 2019

(54) ZYGOMATIC ELEVATOR DEVICE AND METHODS

(75) Inventor: Raymond M. Dunn, Shrewsbury, MA (US)

(73) Assignee: University of Massachusetts, Boston, MA (US)

(*) Notice: Subject to any disclaimer, the term of this patent is extended or adjusted under 35 U.S.C. 154(b) by 0 days.

(21) Appl. No.: 13/582,279

(22) PCT Filed: Mar. 4, 2011

(86) PCT No.: PCT/US2011/027161
§ 371 (c)(1),
(2), (4) Date: Aug. 31, 2012

(87) PCT Pub. No.: WO2011/109696
PCT Pub. Date: Sep. 9, 2011

(65) Prior Publication Data
US 2012/0330368 A1 Dec. 27, 2012

Related U.S. Application Data

(60) Provisional application No. 61/310,950, filed on Mar. 5, 2010.

(51) Int. Cl.
*A61B 17/02* (2006.01)
*A61B 17/88* (2006.01)

(52) U.S. Cl.
CPC ........ *A61B 17/8866* (2013.01); *A61B 17/025* (2013.01); *A61B 17/0218* (2013.01); *A61B 17/885* (2013.01)

(58) Field of Classification Search
CPC ..... A61B 17/02; A61B 17/025; A61B 17/885; A61B 17/8866; A61B 2017/681;
(Continued)

(56) References Cited

U.S. PATENT DOCUMENTS 854,898 A * 5/1907 Lorenz ........................... 84/466
990,277 A * 4/1911 Lauderdale .................... 433/89
(Continued)

FOREIGN PATENT DOCUMENTS

DE    80 00 330 U1   6/1984
DE    295 20 571 U1  2/1996
(Continued)

*Primary Examiner* — Matthew J Lawson
*Assistant Examiner* — Amy R Sipp
(74) *Attorney, Agent, or Firm* — McCarter & English, LLP; Thomas O. Hoover

(57) ABSTRACT

A surgical elevator device that can be used in the reduction of bone fractures, particularly facial bone fractures, and even more particularly zygomatic arch fractures. The elevator device enables accurate measurement of the depth of insertion of the device into tissue space and provides tactile control of fracture location and reduction. In one embodiment, the elevator device comprises a groove on an elevator element for receiving a bone structure. The groove can be formed by a pair of parallel ridges. A projection extending from the elevator provides a pivot point for applying a controlled force to the bone to reduce the fracture. A preferred embodiment further comprises a method of reducing a bone fracture, such as a zygomatic arch fracture.

22 Claims, 5 Drawing Sheets

(58) Field of Classification Search
CPC ............ A61B 17/0218; A61B 17/0281; A61B 17/66–17/666; A61B 2017/0256–2017/0275
USPC ................ 600/201, 210, 217, 226, 235–238; 606/86 R, 87, 90, 105; D8/88, 89; 157/1.3
See application file for complete search history.

(56) References Cited

U.S. PATENT DOCUMENTS

| | | | |
|---|---|---|---|
| 3,863,627 A * | 2/1975 | Bouffard ........................ | 600/210 |
| 4,153,053 A * | 5/1979 | Figallo E ....................... | 606/100 |
| 4,232,660 A * | 11/1980 | Coles ............................. | 600/210 |
| 4,995,875 A * | 2/1991 | Coes ............................. | 606/90 |
| 5,282,816 A * | 2/1994 | Miller et al. .................. | 606/167 |
| 5,363,841 A * | 11/1994 | Coker ................... | A61B 17/0206 600/211 |
| 5,846,192 A * | 12/1998 | Teixido .......................... | 600/210 |
| 5,971,920 A * | 10/1999 | Nagel ............................. | 600/206 |
| 6,299,617 B1 * | 10/2001 | Stamler .......................... | 606/107 |
| 6,322,499 B1 * | 11/2001 | Evans et al. .................. | 600/212 |
| 6,428,472 B1 * | 8/2002 | Haas ............................. | 600/206 |
| 6,482,152 B2 * | 11/2002 | Kim .............................. | 600/210 |
| 6,805,666 B2 * | 10/2004 | Holland et al. ............... | 600/212 |
| 6,817,978 B2 * | 11/2004 | Holland et al. ............... | 600/212 |
| 7,108,698 B2 * | 9/2006 | Robbins et al. ............... | 606/90 |
| 7,195,589 B1 * | 3/2007 | Masson et al. ................ | 600/203 |
| 7,226,413 B2 * | 6/2007 | McKinley ...................... | 600/210 |
| 7,261,689 B2 * | 8/2007 | Holland et al. ............... | 600/212 |
| 8,297,972 B2 * | 10/2012 | Gordon et al. ................ | 433/140 |
| 8,709,036 B2 * | 4/2014 | Picha Muthu et al. ....... | 606/205 |
| 8,740,943 B2 * | 6/2014 | Zucherman et al. ......... | 606/249 |
| 8,747,306 B1 * | 6/2014 | Ramos .......................... | 600/194 |
| 8,900,320 B2 * | 12/2014 | Frederick et al. ........... | 623/22.32 |
| 8,920,426 B2 * | 12/2014 | Henderson ..................... | 606/87 |
| 8,926,664 B1 * | 1/2015 | Millhouse et al. ............ | 606/246 |
| 9,033,874 B2 * | 5/2015 | Murphy ......................... | 600/226 |
| 2002/0165550 A1 * | 11/2002 | Frey et al. ..................... | 606/85 |
| 2003/0139651 A1 * | 7/2003 | Holland ............ | A61B 17/00008 600/245 |
| 2009/0198240 A1 * | 8/2009 | Kaufman ........................ | 606/90 |
| 2011/0190591 A1 * | 8/2011 | Palmer et al. ................. | 600/226 |
| 2013/0211201 A1 * | 8/2013 | Wongsiri ............... | A61B 17/02 600/202 |
| 2014/0012270 A1 * | 1/2014 | Fossez et al. .................. | 606/90 |
| 2014/0343588 A1 * | 11/2014 | Nakamura .................... | 606/170 |

FOREIGN PATENT DOCUMENTS

| | | |
|---|---|---|
| NL | 7 704 151 A | 10/1978 |
| RU | 2 187 260 C1 | 8/2002 |

* cited by examiner

ZYGOMATIC ELEVATOR DEVICE AND METHODS

CROSS REFERENCE TO RELATED APPLICATIONS

This application is 35 USC § 371 national stage filing of International Application No. PCT/US2011/027161, filed Mar. 4, 2011, which claims the priority of U.S. Provisional Application No. 61/310,950, filed on Mar. 5, 2010, the entire teachings of which are incorporated herein.

BACKGROUND OF THE INVENTION

The zygomatic arch is a bone structure located in the cheek area of the face that extends between the zygoma and the temporal bone. Because of the position and prominence of this structure, fractures of the zygomatic arch are a relatively common type of facial injury.

To treat zygomatic arch fractures, various techniques are used to re-set or "reduce" the fracture, by restoring the injured structure to its normal anatomic position. In some cases, this can be done non-invasively by a "closed reduction," in which the bone is restored by external manipulation without requiring an incision. Frequently, however, an "open reduction" is needed, which requires a surgical incision for reduction, and optional internal fixation, of the fractured zygomatic arch.

One common technique for reduction of a zygomatic arch fracture, known as the Gillies' method, involves making a small incision in the skin of the patient's head, preferably behind the hairline to minimize visible scarring, inserting a surgical elevator device behind the fractured bone, and applying a force against the bone to reduce the arch. Other similar techniques are known that involve inserting a surgical instrument, such as a bone hook, wire, towel clip, or similar device, and applying an outward force against the zygomatic arch to reduce the fracture.

SUMMARY OF THE INVENTION

The present invention comprises a surgical elevator device that can be used in the reduction of bone fractures, particularly facial bone fractures, and even more particularly zygomatic arch fractures. The present elevator device enables accurate measurement of the depth of insertion of the device into position adjacent the skeletal feature of interest, provides tactile control of fracture location and reduction, and permits improved control of the magnitude and direction of the force applied to reduce fractures.

In the existing techniques for reduction of zygomatic arch fractures, using a Rowe zygoma elevator, a bone hook or the like, the successful outcome of the procedure is largely dependent on the skill and technique of the surgeon performing the procedure. With existing techniques, it is often difficult to correctly control the location of the elevator device relative to the fracture, as well as the magnitude and direction of the force applied to reduce the fracture.

According to one embodiment of the present invention, a surgical elevator device comprises a elevator element that is inserted under the bone, the elevator element having a distal end and a proximal end, an upper surface. A handle for gripping the elevator device is attached to the proximal end of the elevator element. A groove for receiving a bone structure, the groove being located on a first (upper) surface of the distal portion of the elevator element portion; and a base on a second surface of the elevator device. The groove can be formed by a pair of projections, such as parallel ridges on the first elevator surface, and can provide the surgeon with tactile control of the fracture location in relation to the elevator element. The base can extend substantially unidirectionally from the second surface of the elevator, such as the bottom surface of the elevator element, and provides a pivot point for rotation about an axis to enable the transfer of a controlled force from the handle portion to a bone structure within the groove. In one preferred embodiment, the groove is configured and sized to receive a portion of a zygomatic arch, and the controlled force directed away from the patent comprises a lateral outward force to reduce a zygomatic arch fracture. The base can be configured to be placed against an extraoral anatomic feature, such as the temporal bone of the patent to provide a fulcrum.

In further embodiments, the elevator device includes markings on the elevator element to indicate the depth of insertion of the elevator element into a subject. The portion can include a roughened surface, such as serrations, on the distal end to help prevent the elevator element from slipping against the bone structure. The handle portion is preferably oriented at an angle with respect to the elevator element.

According to yet another embodiment, a method of reducing a fractured bone using a surgical elevator device comprises making an incision over the temporal bone to enable percutaneous insertion of the elevator element into a subject by manipulating a handle portion of the elevator device; positioning a distal end of the elevator element beneath the fractured bone so that the bone is received by a groove on the first surface; positioning a base extending from a surface of the elevator device against an (extraoral) external surface feature of the subject to provide a pivot point; and rotating the handle towards the subject, using the projection as a pivot, to transfer a substantially lateral outward force to the fractured bone positioned in the groove to reduce the fracture. The user, such as a surgeon, can simultaneously palpate the external surface of the tissue overlying the bone. In a preferred embodiment, the fractured bone comprises a zygomatic arch.

BRIEF DESCRIPTION OF THE DRAWINGS

Various aspects of at least one embodiment of the present invention are discussed below with reference to the accompanying figures. In the figures, which are not intended to be drawn to scale, each identical or nearly identical component that is illustrated in the various figures is represented by a like numeral. For purposes of clarity, not every component may be labeled in every drawing. The figures are provided for the purposes of illustration and explanation and are not intended as a definition of the limits of the invention. In the figures.

DETAILED DESCRIPTION OF THE INVENTION

Figure 1:
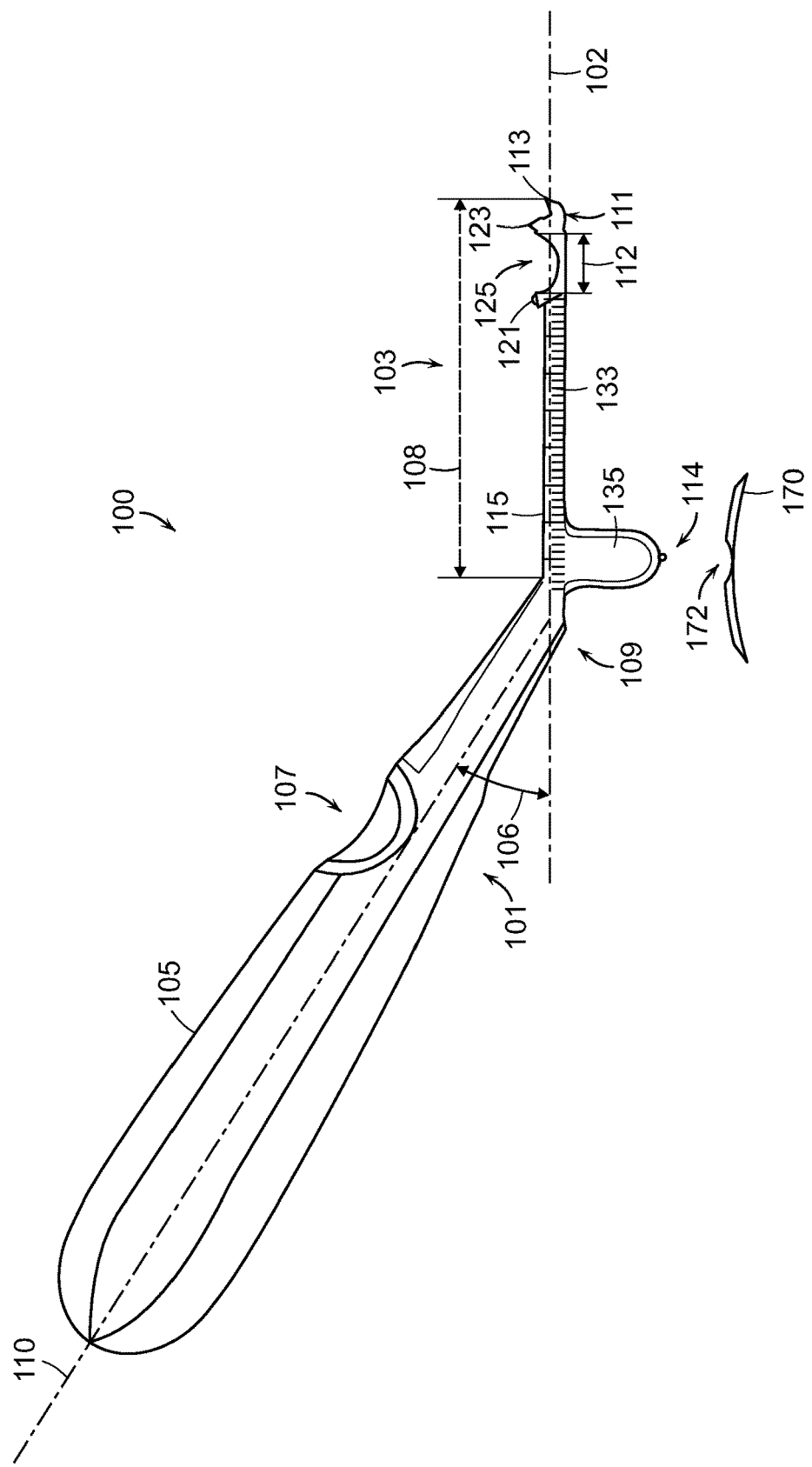
FIG. 1 is a side view of an elevator device according to one embodiment of the invention.
Figure 2:
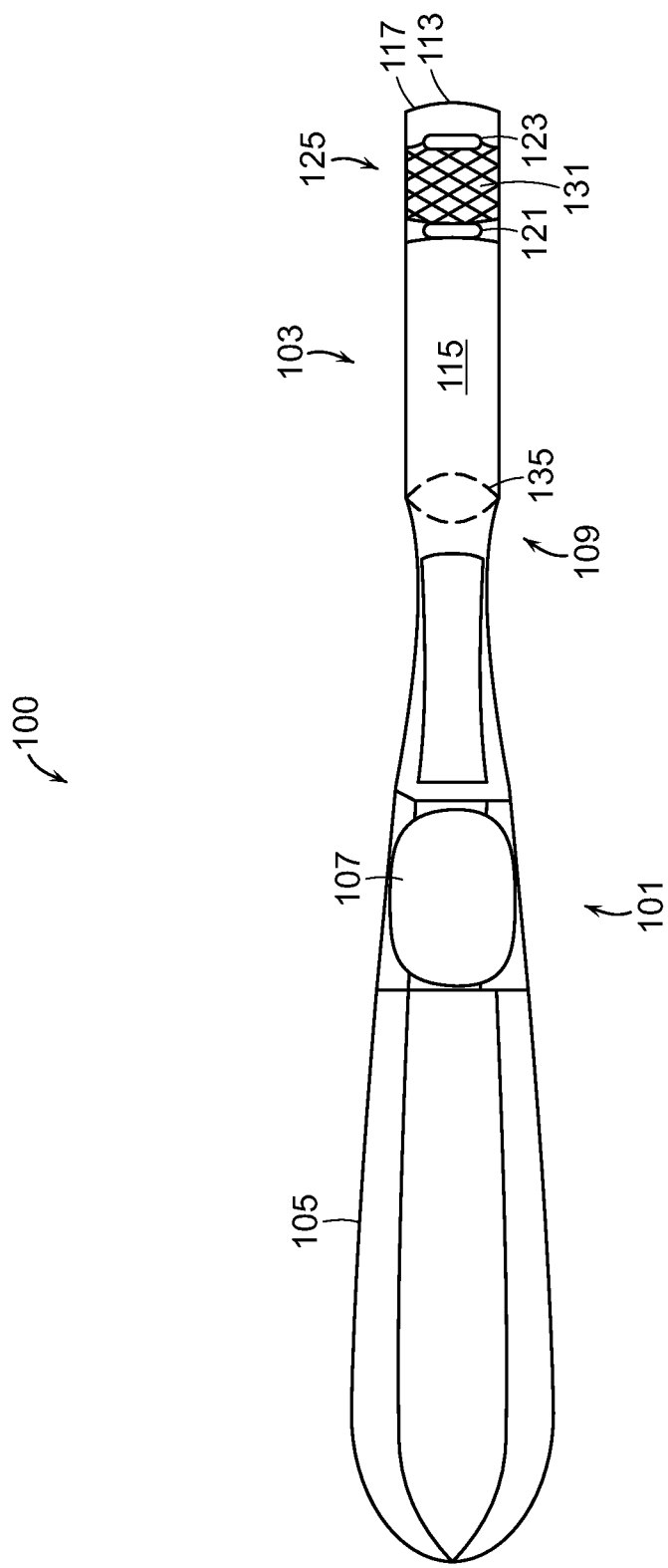
FIG. 2 is a top view of the elevator device of FIG. 1.

Referring now to FIGS. 1-4B, an elevator device 100 for use in a surgical procedure, for instance, for the reduction of a zygomatic arch fracture, is illustrated. The elevator device 100 generally includes a handle portion 101 and a elevator element 103. The elevator element portion 103 can be angled with respect to the handle portion 101, such as shown in the side-view of FIG. 1. This angle 106 can be between 20 and 70 degrees, preferably in a range of 30 to 60 degrees. The angle 106 between the handle axis 110 and the elevator axis 102 is thus preferably at least 20 degrees to provide sufficient clearance from the head of the user. The handle portion 101 can include a grip 105 that allows the device 100 to be easily grasped and manipulated by a user. The grip 105 can further include a groove 107 that is positioned to receive the thumb of a user for more precise control of the device 100.

The elevator element 103 includes a proximal end 109, where the element 103 connects to the handle portion 101, and a distal end 111 terminating at a tip 113. The portion 103 can have a generally flat upper surface 115. The upper surface 115 of the portion 103 is generally between about 40 and 60 mm in length, and in one embodiment is about 50 mm in length. Several different lengths can be housed in a kit for use with different feature sizes. As is illustrated in the top view of FIG. 2, the width of the portion 103 has a length 108 that is generally between about 10 and 15 mm, and in one embodiment is about 12 mm. The sides of the tip 113 can be rounded over as shown in FIG. 1, and form a slightly-curved edge 117 (FIG. 2) where the tip 113 meets the distal end of the flat upper surface 115. The tip 113 can have a sharp edge to aid with insertion.

Figure 3A:
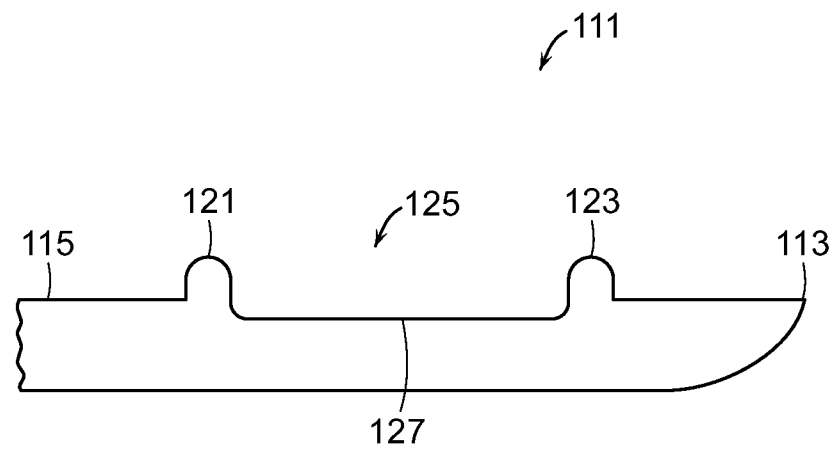
FIG. 3A is a side view of the tip end of the elevator device.
Figure 3B:
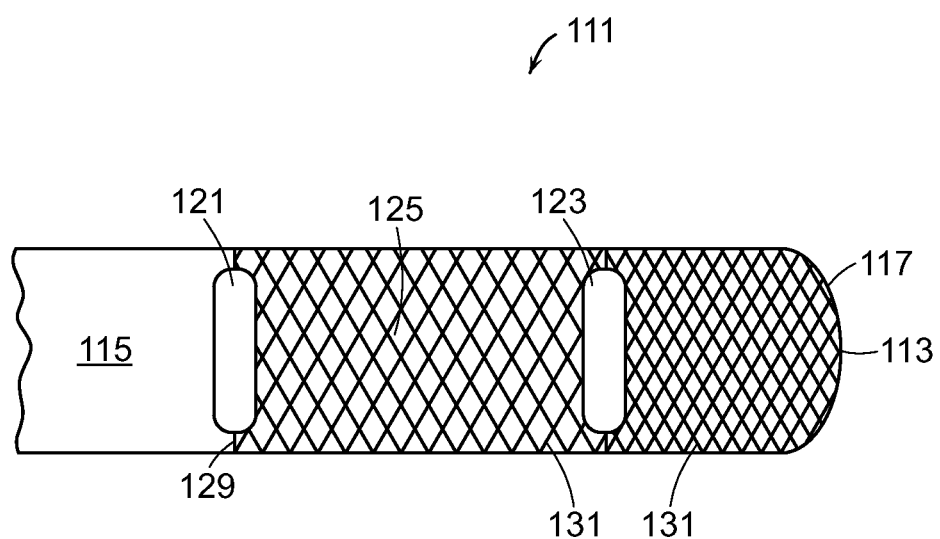
FIG. 3B is a top view of the tip end of the elevator device.

FIGS. 3A and 3B are side and top views, respectively, of the distal end 111 of the portion 103, showing several features of the elevator device 100 in greater detail. The upper surface 115 of the portion 103 include a pair of parallel raised ridges 121, 123. The ridges 121, 123 define a groove 125 that is preferably sized and shaped to receive an anatomical structure, such as the bone or bone fragments of a fractured zygomatic arch. The ridges 121, 123 and the groove 125 can help stabilize the anatomical structure while the elevator 100 is used to apply an outward lateral force against the structure. In one embodiment, the groove 125 further includes a depression 127 in the upper surface 115 of the elevator element. The depression 127 can extend over the entire groove 125 region between the ridges 121, 123, as shown in FIG. 3A.

The ridges 121, 123 can extend across the entire width of the elevator portion 103, or, as shown in FIG. 3B, the ridges 121, 123 can extend over a portion of the width of the portion. In the embodiment of FIGS. 3A and 3B, for example, the ridges 121, 123 are each between about 6 and 10 mm in length, with a gap 129 of between about 1 and 2 mm between the end of each ridge 121, 123 and the edge of the blade portion 103. The proximal ridge 121 (i.e., closest to the handle portion 101) is preferably located about 5 to 10 mm from the tip 113 of the elevator portion 103, and the distal ridge 123 (i.e., closest to the blade tip 113) is preferably about 1 to 4 mm from the tip 113.

The upper surface 115 of the portion 103 preferably includes serrations 131 or a similar surface roughening extending over at least the distal end 111 of the portion 103. The serrations 131 preferably extend at least over the surface of the groove 125 between the ridges 121, 123, and preferably also extend from the distal ridge 123 to the tip 113 of the portion 103. The groove 125 can have a length 112 generally in a range of 2-8 mm. The serrations 131 increase the surface area of the elevator element and increase the frictional forces between the elevator and any tissue or anatomical structures contacting the elevator, and thus helps prevent the elevator from slipping relative to an anatomical structure, such as a zygomatic arch, during a surgical procedure, such as a fracture reduction. As shown in FIG. 3B, the serrations 131 can be in two sections, with a first serrated surface in the groove 125, and a second surface having finer serrations proximate the tip 113.

The elevator device 100 can further include markings 133, such as metric units (millimeters) on the portion 103 of the device, as shown in FIG. 1, that can aid the user in determining the depth of insertion when the elevator device 100 is inserted into a patient.

Figure 4A:
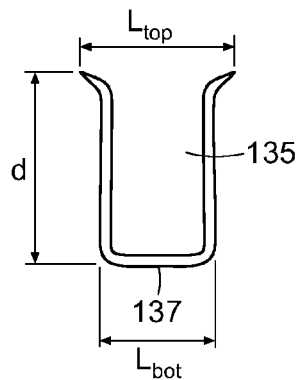
FIG. 4A illustrates a projection of an elevator device of the invention.
Figure 4B:
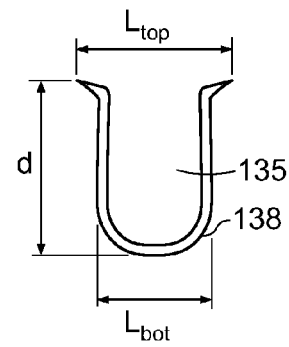
FIG. 4B illustrates an alternative embodiment of the projection.

Turning now to FIGS. 1 and 4A, according to one embodiment, the elevator device 100 includes a projection 135 that extends from the bottom side at a proximal end of the elevator portion 103. In a preferred embodiment, the projection can extend "unidirectionally," meaning that where the upper surface 115 of the blade portion 103 defines a plane, the projection 135 extends in one direction relative to the plane. Conversely, the handle portion 101 can extend unidirectionally in an opposite direction relative to the plane. The projection 135 is preferably located at or near the proximal end 109 of the portion 103. The projection 135 can be a ridge structure with a substantially rectilinear cross-section, such as shown in FIGS. 1 and 4A. In other embodiments, such as shown in FIG. 4B, the projection 135 can comprise a generally curved surface 138 extending from the bottom of the portion 103. Other shapes can be used for the projection 135.

The projection 135 can extend down from the portion 103 a distance, d, of between about 8 and 15 mm, and preferably about 12-14 mm. The projection 135 can have a width of between about 6 and 15 mm, and preferably extends across most or all of the width of the portion 103, as shown in phantom in FIG. 2. In the embodiment of FIG. 4A, the generally flat bottom surface of the projection 135 with area 137, has a length, $L_{bot}$, that is between about 5 and 15 mm, and is preferably about 8 mm. The projection 135 can be tapered to be wider at its top, where the projection 135 meets the portion 103, and narrower at its bottom surface. In the embodiment of FIGS. 1 and 4A, for example, the projection 135 can have a length, $L_{top}$, of about 5 and 20 mm long at its top, and is preferably about 11 mm.

According to one aspect, the projection 135 comprises a unidirectional member that provides a fulcrum, such that by rotating the handle portion 101 in a first direction, with the end 114 of the projection 135 serving as a fixed pivot point, the distal end 111 of the elevator element 103 is caused to move in an arcuate motion in a second, opposing direction. An advantage of this design is that during an invasive medical procedure, such as reduction of a zygomatic arch fracture, the user is able to more precisely control the magnitude and direction of the outward lateral force applied to the patient by the elevator device 100.

Figure 5A:
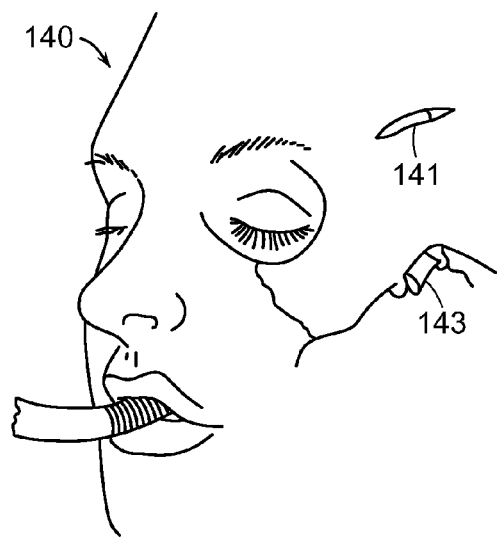
FIGS. 5A and 5B illustrate a surgical procedure using the elevator device of the invention to reduce a zygomatic arch.
Figure 5B:
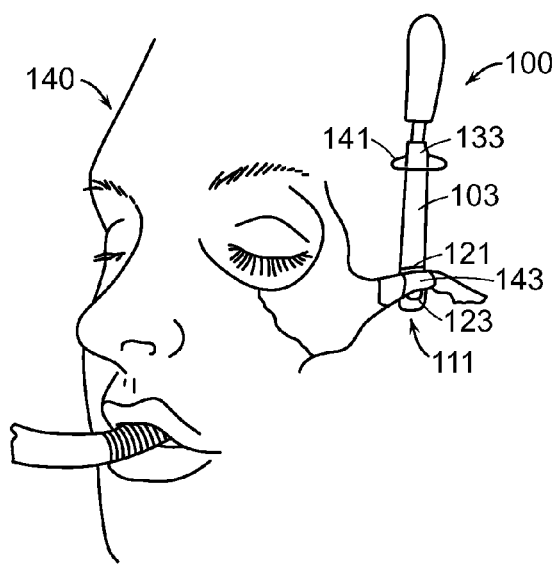

FIGS. 5A and 5B illustrate the elevator device 100 of the present invention being used for a medical procedure, specifically, a reduction of a zygomatic arch fracture. As shown in FIG. 5A, a small incision 141 (e.g., 2 cm) is made in the skin of a patient 140 in the vicinity of the fractured zygomatic arch 143, as is known in standard medical techniques for reduction of a zygomatic arch fracture (e.g., the Gillies' method, etc.). The incision is preferably made percutaneously on an external surface on the side of the patient's head, for example, in the temporal fossa or orbital regions. In one embodiment, a temporal incision is made through the superficial fascia and subcutaneous tissue and into the deep temporal fascia that overlays the temporalis muscle. The superficial fascia and subcutaneous tissue can be retracted. An incision can be made through the deep temporal fascia to expose the temporalis muscle and the temporal bone.

Figure 6:
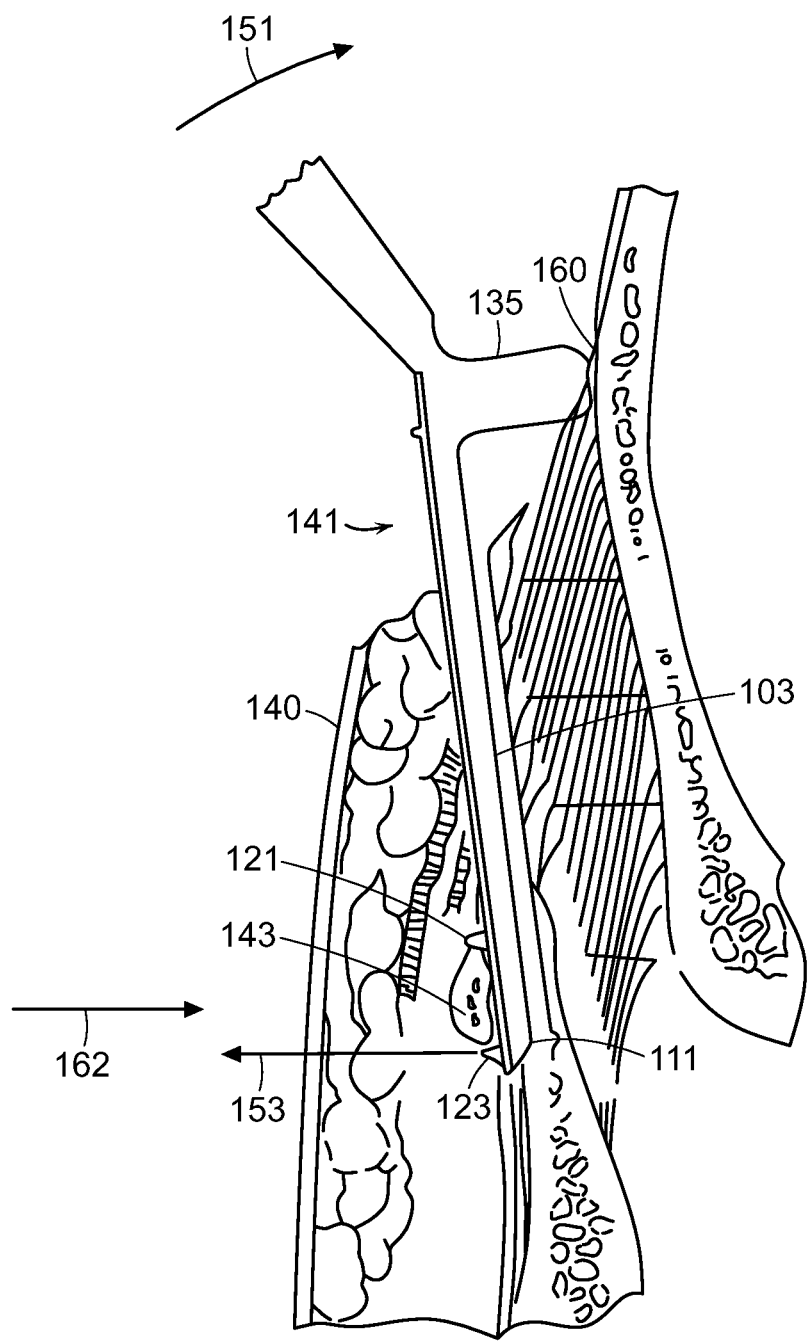
FIG. 6 illustrates a cross-sectional view of a preferred embodiment of an elevator device used to reduce a zygomatic arch fracture.

Next, as shown in FIG. 5B, the elevator device 100 of the present invention is inserted through the incision 141, with the surgeon manipulating the device 100 until the distal end 111 of the portion 103 is positioned between the fractured bone and the underlying anatomy. In one embodiment, the elevator device 100 passes between the deep temporal fascia and the underlying temporalis muscle and temporal bone. The distal end 111 of the elevator passes between the zygomatic arch and the coronoid process. The surgeon can use manual palpitation of the arch structure 143 to determine its position relative to the incision 141 point, and the graduated markings 133 on the elevator device 100 can determine the depth of insertion of the elevator device and consequently aid the surgeon in properly positioning the distal end 111 of the portion 103 under the fractured bone. As shown in FIG. 6, the elevator device 100 is positioned such that the fractured arch 143 lies between the parallel ridges 121, 123 of the elevator, and is received within the groove 125 formed between the ridges 121, 123. The ridges 121, 123 can further provide the surgeon with a tactile feedback of the position of the elevator with respect to the fractured bone. The serrations 131 (FIG. 3B) can help prevent the blade and bone from sliding relative to one another.

To reduce the fracture, the surgeon places the projection 135 against an anatomic feature of the patient, and rotates the handle portion 101 downwards (i.e., towards the patient). In a preferred embodiment, the projection 135 is placed against an extraoral anatomic feature of the patient, such as a bone or muscle. In one embodiment, the projection 135 is placed against the temporal bone at 160 where the incision 141 has exposed a portion thereof. The projection 135 acts as a fixed pivot point, and transfers the force of the rotation of the handle portion 101 towards the patient (see arrow 151) into a substantially lateral outward force (see arrow 153) at the distal end 111 of the portion 103. The substantially lateral outward force 153 of the portion 103 acts on the arch structure 143 to reduce the fracture. The surgeon can manually exert a counterforce 162 to the same region to control the application of force. The size of the surface area on the bottom of projection 135 can be enlarged to distribute the force. A separate plate 170 can be placed over the incision with a recess 172 to receive the base projection 135 which distributes the force to a larger area. After the fracture is reduced, the elevator device 100 is withdrawn through the incision 141, and the incision 141 can be closed.

Although the present elevator device is described herein in connection with the reduction of a zygomatic arch fracture, it will be understood that the present elevator device can be used for other surgical procedures on human and non-human (mammalian) subjects.

The elevator device 100 of the present invention can be made of one or more surgical-grade materials, including a metal such as stainless steel, for example which can be readily sterilized for further use. Alternatively, the device can be made of a rigid plastic material and disposed of after a single use. In a preferred embodiment, the elevator device 100 can be a single, unitary piece, Alternatively, the elevator device 100 can be assembled from a plurality of separate components to provide a composite structure, such as a plastic handle, to facilitate gripping thereof by the hand of the surgeon which can be detached for use with different size elevator elements.

While the invention has been described in connection with specific methods and apparatus, those skilled in the art will recognize other equivalents to the specific embodiments herein. It is to be understood that the description is by way of example and not as a limitation to the scope of the invention and these equivalents are intended to be encompassed by the claims set forth below.

I claim:

1. A surgical zygomatic elevator device, comprising:
    an elevator element having a distal end, a proximal end, an upper surface between the distal end and the proximal end having a length between about 40 mm and 60 mm and a first axis extending longitudinally through the elevator element, the elevator element having a size for insertion through a surgical incision;
    a handle sized to manually grasp the elevator device, the handle being positioned at the proximal end of the elevator element, the handle having a second axis that extends longitudinally through the handle, the handle being positioned at an oblique angle extending above the first axis of the elevator element;
    a groove configured to receive a zygomatic bone structure of a patient, the groove being located on the upper surface of the elevator element and having at least one ridge spaced from the distal end of the elevator element; and
    a projection extending between about 8 mm and 15 mm from a bottom surface of the elevator element, the projection being positioned at a proximal portion of the elevator element that is spaced apart from the groove, the projection being configured to contact an anatomical structure to provide a pivot point such that the elevator element can impart a controlled force in a first direction on the zygomatic bone structure that is positionable within the groove and the projection imparts a second force to the anatomical structure.

2. The surgical elevator device of claim 1, wherein the at least one ridge further comprises a pair of parallel ridges on the upper surface of the elevator element, a gap between the parallel ridges forming the groove.

3. The surgical elevator device of claim 2, wherein the gap is configured to receive a zygomatic arch structure.

4. The surgical elevator device of claim 1, wherein the upper surface comprises a flat plane and a depressed surface region of the elevator element that forms the groove.

5. The surgical elevator device of claim 1, wherein the projection has a substantially rectilinear cross-section.

6. The surgical elevator device of claim 1, wherein the projection has a substantially curved cross-section.

7. The surgical elevator device of claim 1, further comprising markings on the elevator element to indicate a depth of insertion of the elevator device into a mammalian subject.

8. The surgical elevator device of claim 1, wherein the elevator element has a width of between about 10 and 15 mm.

9. The surgical elevator device of claim 1, wherein the groove is less than about 10 mm from a tip of the elevator element.

10. The surgical elevator device of claim 1, wherein the first axis has an angle of at least 20 degrees with respect to the second axis extending through the handle.

11. The surgical elevator device of claim 1, wherein the elevator element includes a rough surface region over at least the distal end of the elevator element.

12. The surgical elevator device of claim 11, wherein the rough surface region comprises serrations.

13. The surgical elevator device of claim 1, wherein the device is insertable into a mammalian body, and the controlled force comprises a lateral outward force for reducing a zygomatic bone fracture.

14. The surgical elevator device of claim 1, wherein the projection extends from the bottom surface at the proximal end of the elevator element.

15. The surgical elevator device of claim 1, wherein the elevator device is an extraoral surgical device.

16. The surgical elevator device of claim 15, wherein the projection is configured to be placed against an extraoral anatomic feature of a patient to provide a fulcrum.

17. The surgical elevator device of claim 16, wherein the extraoral anatomic feature comprises an orbital region.

18. The surgical elevator device of claim 1, wherein the projection is placed to press against a temporal bone.

19. The surgical elevator device of claim 1, wherein the handle extends at an angle relative to the elevator element, and in a direction opposite the direction of the projection relative to a plane of the upper surface.

20. The device of claim 1 wherein the projection is positioned at the proximal end of the elevator element such that the projection is placed to press against a temporal bone.

21. A zygomatic elevator device, comprising:
an elevator element having a distal end, a proximal end, an upper surface between the distal end and the proximal end having a length between about 40 mm and 60 mm and a first axis extending through the elevator element;
a handle sized to manually grasp the elevator device, the handle being positioned at the proximal end of the elevator element, the handle having a second axis positioned at an oblique angle extending above the upper surface of the elevator element;
a groove configured to receive a zygomatic bone structure, the groove being located on the upper surface of the elevator element, and having at least one ridge spaced from the distal end of the elevator element by a predetermined distance;
a projection extending between about 8 mm and 15 mm from a bottom surface of the elevator element, the projection being proximal to, and spaced from, the groove, wherein the projection is positioned at a proximal portion of the elevator element and configured to contact an anatomical structure that is separated from the groove by a distance to provide a pivot point such that the elevator element can impart a force on the zygomatic bone structure that is positionable within the groove while the projection imparts a second force to the anatomical structure.

22. The device of claim 21 further comprising a second ridge parallel to the at least one ridge, wherein a gap between the at least one ridge and the second ridge forms the groove to receive the zygomatic bone structure.

* * * * *